United States Patent [19]
Hausmann et al.

[11] Patent Number: 5,697,164
[45] Date of Patent: Dec. 16, 1997

[54] MOVABLE POSITIONING AID PERMITTING ABDUCTION AND ROTATION OF THE SHOULDER JOINT FOR A KINEMATIC IMAGING EXAMINATION THEREOF

[75] Inventors: Joerg Hausmann, Erlangen; Klaus Detmar, Nuremberg, both of Germany

[73] Assignee: Siemens Aktiengesellschaft, Munich, Germany

[21] Appl. No.: 552,362

[22] Filed: Nov. 2, 1995

[30] Foreign Application Priority Data

Nov. 18, 1994 [DE] Germany ............... 44 41 046.8

[51] Int. Cl.⁶ ........................................... A61B 6/04
[52] U.S. Cl. ................... 33/512; 128/653.1; 5/601
[58] Field of Search .................. 33/511, 512; 128/653.1; 5/601, 623

[56] References Cited

U.S. PATENT DOCUMENTS

| | | | |
|---|---|---|---|
| 3,020,909 | 2/1962 | Stevens | 5/623 |
| 5,329,924 | 7/1994 | Bonutti | 128/653.1 |
| 5,349,956 | 9/1994 | Bonutti | 128/653.1 |
| 5,520,181 | 5/1996 | Kreidler et al. | 5/601 |
| 5,542,423 | 8/1996 | Bonutti | 5/601 |
| 5,546,942 | 8/1996 | Zhang | 128/653.1 |
| 5,562,094 | 10/1996 | Bonutti | 128/653.1 |

*Primary Examiner*—Thomas B. Will
*Attorney, Agent, or Firm*—Hill, Steadman & Simpson

[57] ABSTRACT

A guide plate, on which a carrier runs in a guide element around a pivot point, is laterally secured to the examination table. An arm rest is arranged at the carrier, this arm rest being rotatable in the carrier around an axis that lies on a line extending between the pivot point and the arm rest.

11 Claims, 6 Drawing Sheets

MOVABLE POSITIONING AID PERMITTING ABDUCTION AND ROTATION OF THE SHOULDER JOINT FOR A KINEMATIC IMAGING EXAMINATION THEREOF

BACKGROUND OF THE INVENTION

1. Field of the Invention

The present invention is directed to a positioning aid suitable for use in assisting in the kinematic imaging examination of a subject in a medical imaging apparatus, and in particular to such a positioning aid which permits abduction and rotation of the shoulder joint.

2. Description of the Prior Art

It is desirable for the dynamic examination of the shoulder joint for this joint to be moved in a reproducible manner. This need especially arises in imaging methods. Nuclear magnetic resonance tomography systems, such as, for example, sold by Siemens AG under the name "Magnetom Open®" are especially suitable for the dynamic examination of the shoulder joint.

SUMMARY OF THE INVENTION

An object of the present invention is to provide a positioning aid that allows abduction and simultaneously allows rotation of the shoulder joint in a reproducible manner.

The above object is achieved in accordance with the principles of the present invention in a positioning aid having a guide plate laterably attachable to a part of the patient support table in a medical imaging apparatus, the guide plate having a guide element, with a carrier disposed on the guide plate so as to be movable around a pivot point on the guide plate, in a path defined by the guide element. An arm rest is disposed in the carrier, the arm rest being rotatable in the carrier around an axis extending between the pivot point and the arm rest.

DESCRIPTION OF THE PREFERRED EMBODIMENTS

Figure 1:
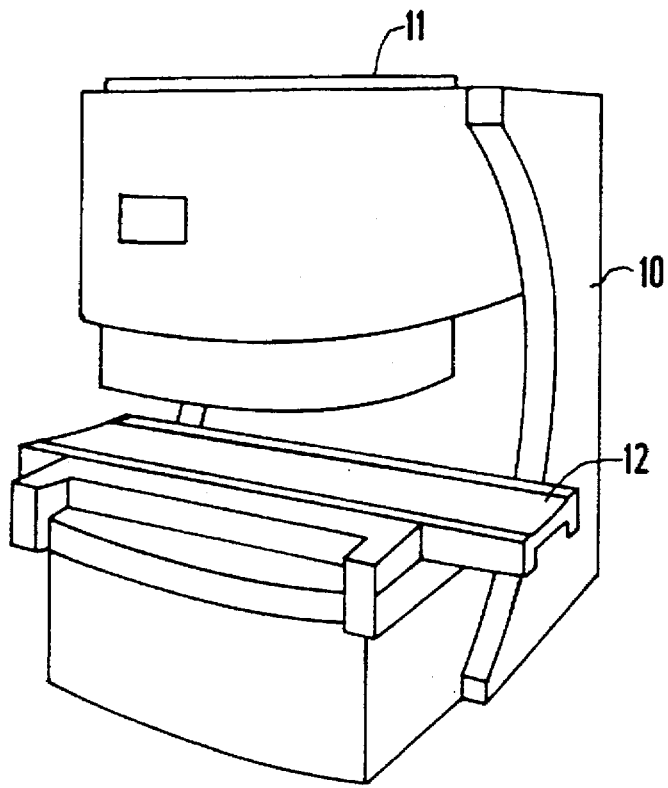
FIG. 1 illustrates the structure of a nuclear magnetic resonance tomography with a C-shaped magnet.

FIG. 1 schematically shows a nuclear magnetic resonance tomography apparatus of the type sold by Siemens AG under the name "Magnetom Open®". The nuclear magnetic resonance tomography apparatus 10 has a C-shaped magnet, so that the examination space remains easily accessible during the examination and the patient being examined has full freedom of motion toward at least one side. This nuclear magnetic resonance tomography apparatus is therefore very well-suited for dynamic examinations. One arm of the patient can be freely moved toward the outside examination of the shoulder joint. The examining physician or technician can perform movements of the patient during the image acquisition without being exposed to a radiation load. The patient can also be instructed to perform unassisted specific arm movements. Exposures of the shoulder joint in different positions have far greater diagnostic utility than purely static examinations in only one position.

The positioning aid set forth below makes it possible to implement, or to have the patient implement, abduction and rotation of the shoulder joint in a reproducible way during an image acquisition procedure.

Figure 2:
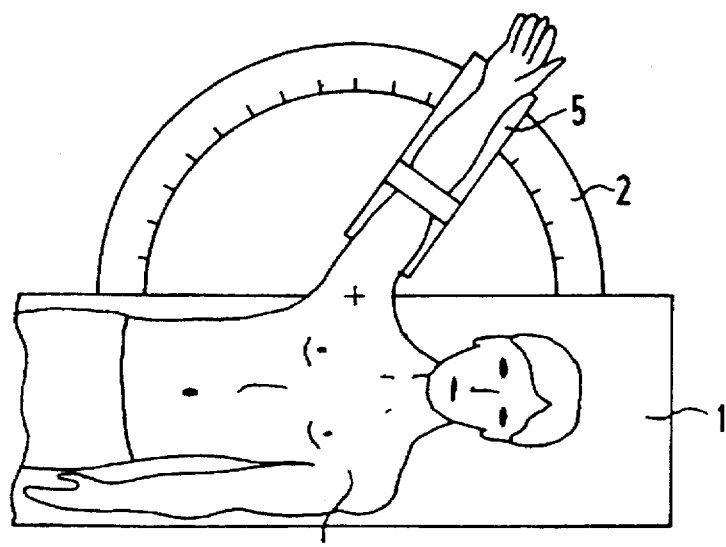
FIG. 2 illustrates the structure of a positioning aid constructed in accordance with the principles of the present invention in a plan view.

The schematic structure of the positioning aid is shown in FIG. 2. A table support 1 on which a patient 13 lies is placed on the patient table 12 according to FIG. 1. A guide plate 2 is attached laterally to the table support 1. An arm rest 5 is guided on this guide plate 2, this arm rest 5 being described in greater detail with reference to the other figures. As schematically indicated by a scale in FIG. 2, this arm rest 5 is movable by about 180° in the plane of the table support 1.

Figure 3:
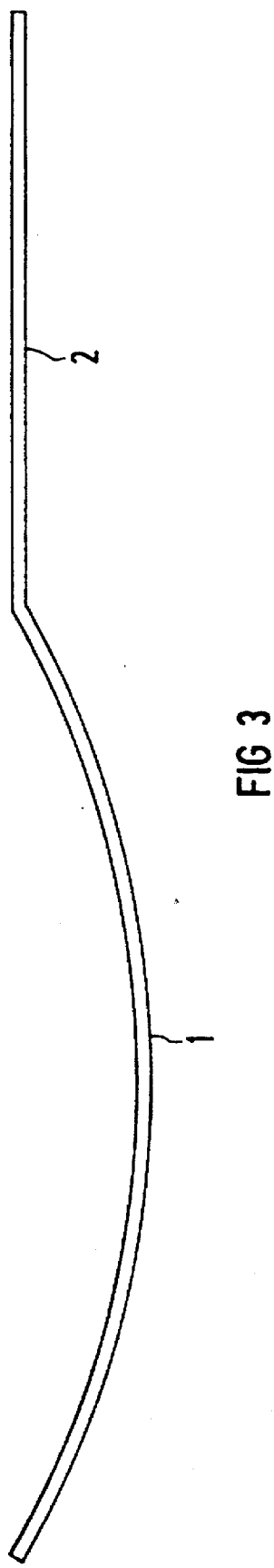
FIG. 3 illustrates the structure of a table support for use with the inventive positioning aid in a sectional view.
Figure 4:
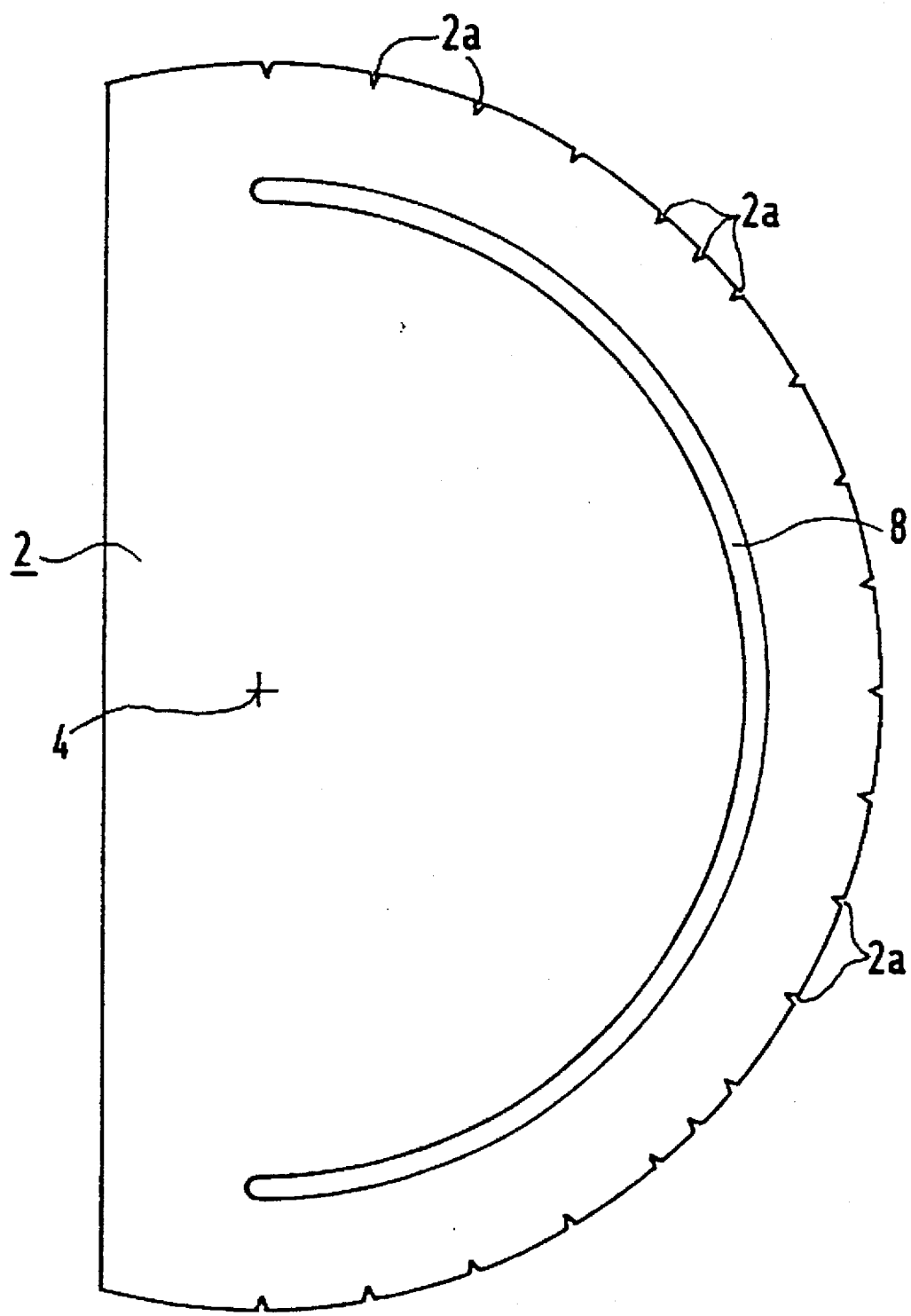
FIG. 4 illustrates the structure of a guide plate of the inventive positioning aid attached to the table support, shown in a plan view.

FIG. 3 shows a front view of the table support 1 with the guide plate 2 attached thereto. FIG. 4 shows a plan view of the guide plate 2. It can be seen that the guide plate 2 has a semicircular shape, with the center of the circle being disposed at a pivot point 4 on which the shoulder joint is positioned during imaging. The guide plate 2 has an approximately semicircular recess 8 forming a guide path, with the midpoint of this semicircle coinciding with the pivot point 4. Recesses 2a in the form of notches are distributed at defined angular positions along the semicircular arc at the outer face of the semicircular guide plate 2.

Figures 9, 10:
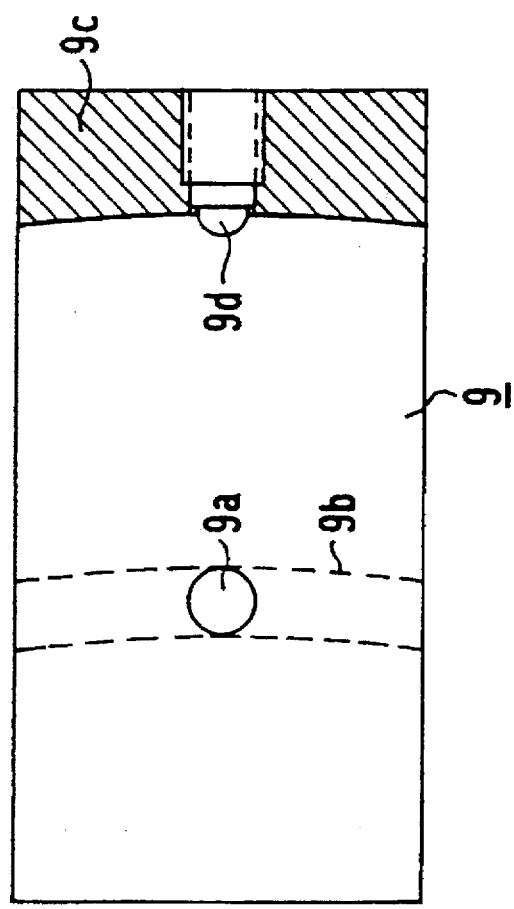
FIG. 9 illustrates the structure of a guide carriage of the inventive positioning aid in a sectional view.
FIG. 10 illustrates the structure of a guide carriage of the inventive positioning aid in a front view.

A guide carriage 9, as shown enlarged in FIGS. 9 and 10, is put in place on the guide plate 2. This guide carriage 9 engages into the recess 8 of the guide plate 2 with a pin 9a. Alternatively, the guide carriage 9 can have an arcuate projection 9b (shown with broken lines in FIG. 9) that slides in the recess 8. The guide carriage 9 has a further projection 9c that engages around the end face of the guide plate 2 and which has an interior shape matched to the arcuate shape of the guide plate 2. A resilient catch element 9d that, dependent on the position of the guide carriage 9, engages into one of the notches 2a of the guide plate 2 is provided in this projection 9c.

FIG. 10 shows the projection 9c with the catch element 9d again in a front view.

Figure 5:
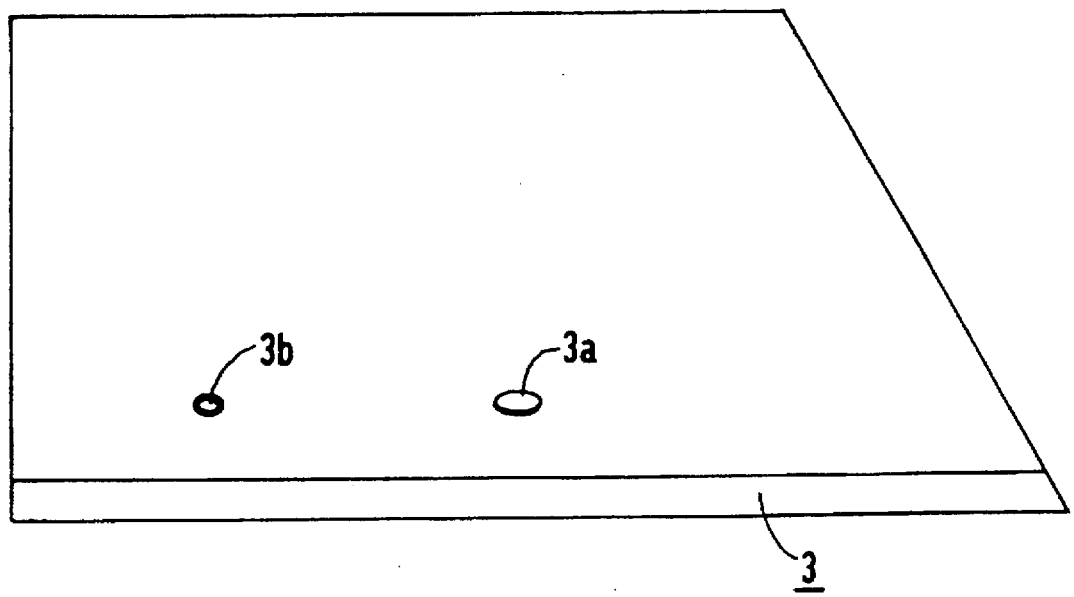
FIG. 5 illustrates the structure of a carrier of the inventive positioning aid in a side view.
Figure 6:
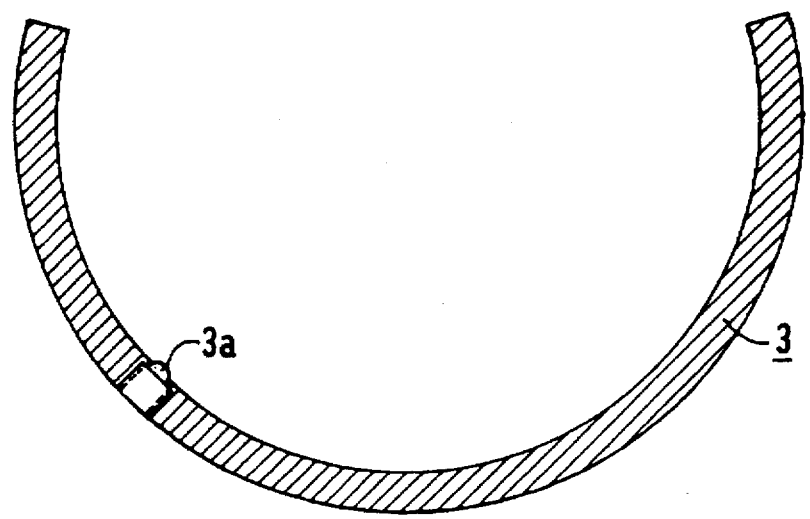
FIG. 6 illustrates the structure of a carrier of the inventive positioning aid in a sectional view.

A carrier 3 that is shown in a front view in FIG. 5 and in section in FIG. 6 is secured on the guide carriage 9. This carrier 3 is generally in the shape of a half shell, with the end disposed away from the pivot point 4 being angled. A resilient catch element 3a that engages in notches of the arm rest (described below) is provided in the carrier 3. A pin 3b is also introduced into the carrier 3; the purpose thereof is described below.

Figure 7:
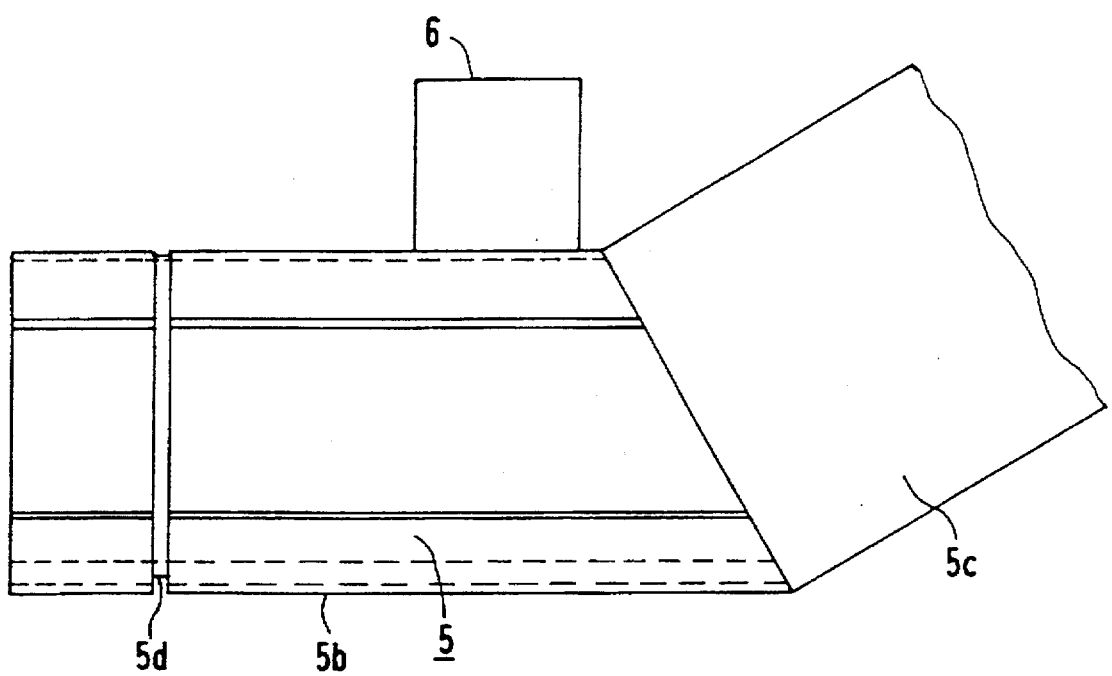
FIG. 7 illustrates the structure of an arm rest of the inventive positioning aid in a side view.
Figure 8:
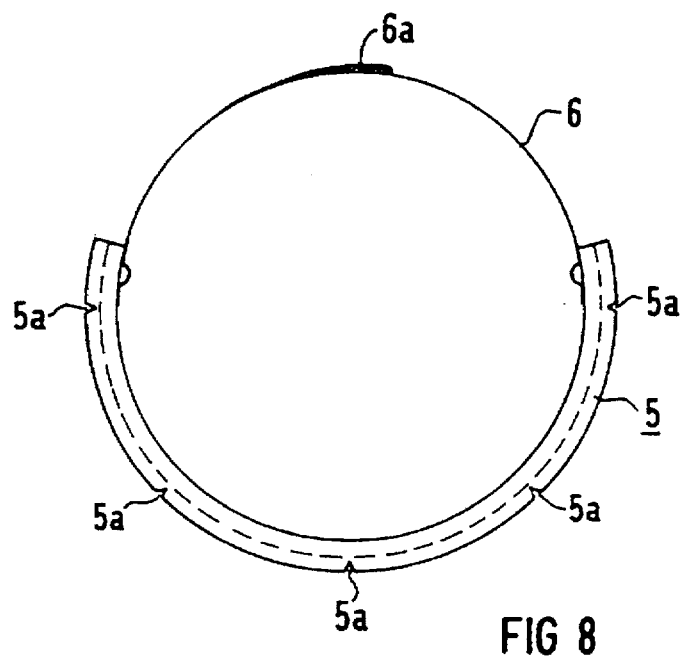
FIG. 8 illustrates the structure of an arm rest of the inventive positioning aid in a front view.

An arm rest 5 shown in plan view in FIG. 7 and from the end in FIG. 8 is introduced into the carrier 3. The arm rest has a part 5b adjacent the guide plate 2 and a part 5c angled with respect thereto. The planar part 5b is intended for accepting the upper arm of a patient; the angled part is intended for accepting the patient's lower arm.

Both the part 5b and the part 5c of the arm rest 5 are in the form of half shells. Catch notches 5a are provided at the outside circumference of the part 5b, the resilient catch element 3a of the carrier 3 engaging into these catch notches 5a in the assembled condition. At its outer circumference, the arm rest 5 also has a channel 5d into which the pin 3b of the carrier 3 engages. This prevents a dislocation of the arm rest 5 in longitudinal direction of the carrier 3. An upper arm of the patient under examination can be fixed in the arm rest 5 with the assistance of a belt 6. The belt 6 is adjustable and can, for example, be a Velcro® fastener 6a.

Motion of the arm in the plane of the guide plate 2 is thus possible with the described positioning aid in the assembled condition. Locked positions are provided in various positions at which the resilient catch element 9d of the guide carriage 9 engages into the recesses 2a of the guide plate 2. Defined positions of the arm can thus be set in a simple way.

At the same time, however, the arm can be moved around its longitudinal axis, with the arm rest 5 then turning in the carrier 3. Various locked positions are thereby also possible, these being defined by the catch notches 5a of the arm rest 5 in conjunction with the resilient catch element 3a of the carrier 3.

No disturbing revolute joints are required in the pivot point of the shoulder joint since the abduction is guided by the recess 8 in the guide plate 2. The shoulder blade itself is expediently fixed during the examination, so that only the desired rotational movements are possible but, for example, no dislocation occurs. The fixing is unproblematically possible because of the lack of a revolute joint; it can, for example, be implemented with a vacuum pillow.

A reproducible abduction and rotation in the shoulder joint are thus possible with the illustrated arrangement. Movement-dependent modifications in the shoulder joint can thus be evaluated extremely well, particularly for the impingement syndrome and the instability of the shoulder joint.

Although modifications and changes may be suggested by those skilled in the art, it is the intention of the inventors to embody within the patent warranted hereon all changes and modifications as reasonably and properly come within the scope of their contribution to the art.

We claim as our invention:

1. A movable positioning aid for permitting kinematic examination of a shoulder joint of an examination subject in a medical imaging apparatus, said medical imaging apparatus having a patient support table and said movable positioning aid comprising:

a guide plate laterably attachable to said patient support table, said guide plate having a non-rotatable guide element defining a guide path;

a carrier mounted exclusively on said guide plate for movement along said guide path defined by said guide element;

an arm rest; and means for temporarily engaging said arm rest in said carrier and for permitting movement of said arm rest in said carrier along said guide path around a non-mechanical anatomical pivot point.

2. A positioning aid as claimed in claim 1 further comprising adjustable fixing means for fastening an upper arm of said patient in said arm rest.

3. A positioning aid as claimed in claim 2 wherein said adjustable fixing means comprises a belt.

4. A positioning aid as claimed in claim 1 wherein said arm rest comprises a first portion disposed adjacent said guide plate for supporting an upper arm of said patient and a second portion, angled relative to said first portion, for supporting a lower arm of said patient.

5. A positioning aid as claimed in claim 1 wherein said guide element comprises a recess in said guide plate forming a circular arc around said pivot point, and said positioning aid further comprising a guide carriage engaging said recess and to which said carrier is mounted.

6. A positioning aid as claimed in claim 5 wherein said guide carriage has a pin extending into said recess for engaging said guide carriage with said guide plate.

7. A positioning aid as claimed in claim 5 wherein said guide carriage comprises a circular arc-shaped projection extending into said recess for engaging said guide carriage and said guide plate.

8. A positioning aid as claimed in claim 5 wherein said guide plate has a semicircular edge having a plurality of notches therein disposed at defined angular positions along said semicircular edge, and said guide carriage having a resilient catch element releasably engageable in a selected one of said notches for temporarily latching said carrier in a selected angular position.

9. A positioning aid as claimed in claim 1 further comprising means for temporarily latching said carrier in a selected one of a plurality of angular positions along a circular arc extending around said pivot point.

10. A positioning aid as claimed in claim 1 wherein each of said carrier and said arm rest comprise an upwardly open circular shell, with said arm rest being nested in said carrier.

11. A positioning aid as claimed in claim 10 comprising means for temporarily engaging said shell of said arm rest in said shell of said carrier in a selected position.

* * * * *